United States Patent [19]

Harde et al.

[11] Patent Number: 5,270,289
[45] Date of Patent: Dec. 14, 1993

[54] HERBICIDAL DIMETHOXY PYRIMIDINYLOXY-FLUORINATED ACIDS AND SALTS

[75] Inventors: Christoph Harde; Erhard Nordhoff; Anita Krüger; Gabriele Krüger; Gerhard Tarara; Peter Wegner; Nikolaus Heinrich; Clemens Kötter; Gerhard Johann; Richard Rees, all of Berlin, Fed. Rep. of Germany

[73] Assignee: Schering Aktiengesellschaft, Fed. Rep. of Germany

[21] Appl. No.: 863,469

[22] Filed: Apr. 1, 1992

Related U.S. Application Data

[63] Continuation of Ser. No. 555,053, Jul. 19, 1990, abandoned.

[30] Foreign Application Priority Data

Jul. 19, 1989 [DE] Fed. Rep. of Germany ....... 3924259
Mar. 22, 1990 [DE] Fed. Rep. of Germany ....... 4009481

[51] Int. Cl.$^5$ .................... A01N 43/54; A01N 43/66; C07D 239/60; C07D 251/30
[52] U.S. Cl. .................... 504/243; 504/227; 504/230; 504/231; 504/232; 504/234; 544/218; 544/219; 544/300; 544/301; 544/302; 544/310; 544/312; 544/313; 544/314; 544/316; 544/317; 544/318
[58] Field of Search .................... 71/92; 544/302; 504/243

[56] References Cited

U.S. PATENT DOCUMENTS

| | | | |
|---|---|---|---|
| 3,940,394 | 2/1976 | Santilli et al. | 544/295 |
| 4,968,340 | 11/1990 | Kaku et al. | 544/302 |
| 5,137,564 | 8/1992 | Jones | 71/92 |
| 5,139,563 | 8/1992 | Astles et al. | 71/92 |

FOREIGN PATENT DOCUMENTS

| | | |
|---|---|---|
| 0223406 | 5/1987 | European Pat. Off. |
| 0249707 | 12/1987 | European Pat. Off. |
| 0249708 | 12/1987 | European Pat. Off. |
| 0287072 | 10/1988 | European Pat. Off. |
| 0287079 | 10/1988 | European Pat. Off. |
| 0347811 | 12/1989 | European Pat. Off. |
| 400741 | 12/1990 | European Pat. Off. |
| 301668 | 12/1989 | Japan ................. 544/302 |
| 3-240777 | 10/1991 | Japan . |

OTHER PUBLICATIONS

Petrenko et al, *Chemical Abstracts*, vol. 106, No. 133734 (1987).
Derwent Abstract for JP 32-40777 (Oct. 28, 1991).

*Primary Examiner*—Emily Bernhardt
*Attorney, Agent, or Firm*—Ostrolenk, Faber, Gerb & Soffen

[57] ABSTRACT

The invention relates to new substituted α-pyrimidinyloxy(thio)- and α-triazinyloxy(thio)carboxylic acid derivatives of general formula I $$\begin{array}{c} R^2 \\ \diagdown \\ Y \diagup\hspace{-2mm}= N \\ \hspace{6mm} \diagdown\hspace{-2mm}-X-\overset{A}{C}-COOR^1 \\ \diagup\hspace{-2mm}= N \\ R^3 \end{array}$$ (I)

in which A, R$^{1-3}$, X and Y have the meanings given in the description, processes for their preparation and their use as herbicides, fungicides and plant growth regulants.

12 Claims, No Drawings

HERBICIDAL DIMETHOXY PYRIMIDINYLOXY-FLUORINATED ACIDS AND SALTS

This is a continuation of application Ser. No. 07/555,053 filed on Jul. 19, 1990 and now abandoned.

DESCRIPTION

This invention relates to new substituted α-pyrimidinyloxy(thio)- and α-triazinyloxy(thio)carboxylic acid derivatives, processes for their preparation and their use as herbicides, fungicides and plant growth regulators.

It is known that pyrimidine derivatives possess herbicidal activity (EP 223 406, 249 707, 249 708, 287 072, 287 079 and 347 811). However, the herbicidal activity of these known compounds is often insufficient or selectivity problems are seen in important crops.

The object of the present invention is to make new compounds that do not have these disadvantages and have improved biological properties over the known compounds.

It has now been found that substituted α-pyrimidinyloxy(thio)- and α-triazinyloxy(thio)carboxylic acid derivatives of general formula I

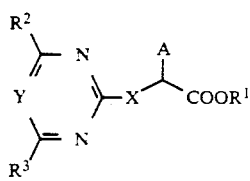

in which

A is one of the groups A-1 to A-6 of general formula

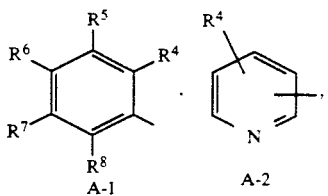

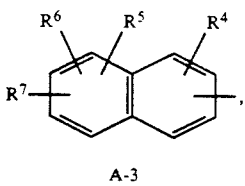

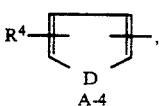

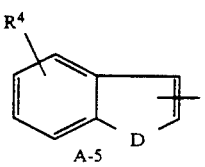

or

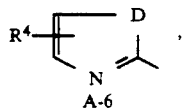

a $C_1$-$C_6$-alkyl or $C_3$-$C_6$-cycloalkyl, both of which are substituted by $C_1$-$C_4$-alkoxy or halogen, a straight-chain $C_2$-$C_6$-alkenyl group, cyclopropyl or a benzyl group, which is substituted on the aliphatic carbon atom by halogen or $C_1$-$C_4$-alkoxy or by methyl and $C_1$-$C_4$-alkoxy or halogen;

D is oxygen, sulphur or the group —$NR^9$—;

$R^1$ is hydrogen, $C_1$-$C_4$-alkyl or benzyl;

$R^2$ and $R^3$, which may be the same or different, are $C_1$-$C_4$-alkyl, $C_1$-$C_4$-alkoxy, $C_1$-$C_4$-alkylthio, $C_1$-$C_4$-alkylamino, di-$C_1$-$C_4$-alkylamino or halogen, with the proviso that when A is unsubstituted phenyl, X is sulphur and Y is methine, $R^2$ and $R^3$ cannot both be methyl or one cannot be methyl when the other is tert-butyl;

$R^4$, $R^5$, $R^6$, $R^7$ and $R^8$, which may be the same or different, are hydrogen, $C_1$-$C_4$-alkyl, $C_1$-$C_4$-alkoxy, amino, di-$C_1$-$C_4$-alkylamino, nitro, halogen, trifluoromethyl or phenyl;

$R^9$ is hydrogen or $C_1$-$C_4$-alkyl;

X is oxygen or sulphur, with the proviso that when X is not oxygen when A is allyl; and Y is methine or nitrogen, with the proviso that Y is not methine when A is 1-chloroethyl or 1-methyl-2,2,2-trifluoroethyl;

as well as their alkali metal, alkaline earth metal and organic ammonium salts, and their optical isomers, show interesting herbicidal, fungicidal and plant growth regulant activity.

The expression "halogen" means fluorine, chlorine, bromine and iodine. By the term alkali metal is meant lithium, sodium or potassium and by the term alkaline earth metal is meant calcium, strontium or barium.

The compounds of the invention of general formula I can be prepared for example

A) by reacting a compound of general formula II

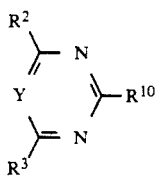

in which $R^2$, $R^3$ and Y have the meanings given under general formula I and $R^{10}$ is halogen, alkylsulphonyl or phenylsulphonyl, with a compound of general formula III

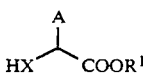

in which A, $R^1$ and X have the meanings given under general formula I, in a suitable solvent in the presence of a suitable base, or B) by reacting a compound of general formula VIII

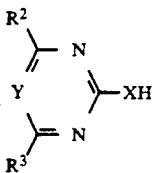

(VIII)

in which $R^2$, $R^3$, X and Y have the meanings given under general formula I, with a compound of general formula IX

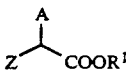

(IX)

in which A and $R^1$ have the meanings given under general formula I and Z is halogen or alkylsulphonyloxy, in a suitable solvent in the presence of a suitable base, or C) by reacting a compound of general formula X

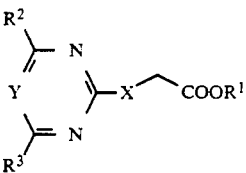

(X)

in which $R^1$, $R^2$, $R^3$, X and Y have the meanings given under general formula I, with a compound of general formula XI $$A-R^{10} \quad (XI)$$

in which $A^1$ has the meanings given under general formula I, with the exception of the groups A-1 to A-6, and $R^{10}$ is halogen, alkylsulphonyloxy or phenylsulphonyloxy, in a suitable solvent in the presence of a suitable base,
and if desired (i) a compound of general formula I in which $R^1$ is hydrogen, $C_1$-$C_4$-alkyl or benzyl, so obtained, is reacted with an alkali metal base or an alkaline earth metal base, in a suitable polar solvent, to give a compound of general formula I in which $R^1$ is an alkali metal atom or one equivalent of an alkaline earth metal atom, (ii) and/or if desired, a compound of formula I in which $R^1$ is an alkali metal atom or one equivalent of an alkaline earth metal atom, is reacted with a suitable acid in a suitable solvent to give a compound of general formula I in which $R^1$ is hydrogen, (iii) and/or if desired, a compound of formula I in which $R^1$ is hydrogen is reacted with a suitable base in a suitable solvent to give a compound of general formula I in which $R^1$ is an alkali metal atom or one equivalent of an alkaline earth metal atom or an organic ammonium group.

The individual process variants are preferably carried out in the presence of a diluent. For this, a solvent which is inert to the reactants is used.

Suitable solvents include water, aliphatic, alicyclic and aromatic hydrocarbons, that can be optionally chlorinated, such as for example hexane, cyclohexane, petroleum ether, ligroin, benzene, toluene, xylene, methylene chloride, chloroform, carbon tetrachloride, ethylene chloride and trichloroethane, ethers, such as for example diisopropyl ether, dibutyl ether, propylene oxide, dioxane and tetrahydrofuran; ketones, such as for example acetone, methyl ethyl ketone, methyl isopropyl ketone, nitriles, such as for example acetonitrile and propionitrile, alcohols, such as for example methanol, ethanol, isopropanol, butanol and ethylene glycol, esters, such as for example ethyl acetate and amyl acetate, amides, such as for example dimethylformamide and dimethylacetamide, sulphones and sulphoxides, such as for example dimethyl sulphoxide, and bases, such as for example pyridine.

The presence of a catalyst can be an advantage. Suitable catalysts include potassium iodide and onium compounds, such as quaternary ammonium, phosphonium and arsonium compounds as well as sulphonium compounds. Also suitable are polyglycol ethers, especially cyclic ethers, such as 18-crown-6, and tertiary amines, such as for example tributylamine. Preferred compounds are quaternary ammonium compounds, such as for example benzyltriethylammonium chloride and tetrabutylammonium bromide.

The reactions can be carried out under atmospheric pressure but if desired higher or lower pressures can be used.

The process variant A) is preferably carried out in an aromatic hydrocarbon, such as benzene, toluene or xylene, a halogenated hydrocarbon, such as methylene chloride or chloroform, an alcohol, such as methanol, ethanol or isopropanol, an ether, such as for example diethyl ether, diisopropyl ether, tetrahydrofuran or dioxane, a ketone, such as for example acetone or methyl ethyl ketone, an ester, such as methyl acetate or ethyl acetate, or a polar aprotic solvent, such as dimethylformamide, dimethylacetamide or dimethyl sulphoxide, or another solvent, such as acetonitrile or water.

Bases that can be used include an alkali metal, such as sodium or potassium, an alkali metal or alkaline earth metal hydride, such as sodium hydride, potassium hydride or calcium hydride, a carbonate, such as sodium carbonate or potassium carbonate, or a metal hydroxide, such as sodium hydroxide or potassium hydroxide.

The reaction is suitably carried out between room temperature and the boiling point of the particular solvent or solvent mixture. The reaction time lies between 1 and 24 hours.

The reaction can also be carried out in the absence of a solvent, at a temperature between 120° and 160° C., by using as alkali metal carbonate, such as anhydrous potassium carbonate.

The preparation of the α-hydroxy or α-mercapto carboxylic acid derivatives used in this process variant can be carried out using the following literature processes: J. Org. Chem. 33, 2565 (1968); J. Amer. Chem. Soc. 95, 7146 (1973); J. Chem. Soc. 1957, 3262; J. Org. Chem. 33, 1831 (1968); Can. J. Chem. 60 (1982) 2707 and Bull. Soc. Chim. Fr. 1969, 2721.

The process variants (i) and (ii) are preferably carried out in an alcohol, such as ethanol, propanol or isopropanol, a ketone, such as acetone or methyl ethyl ketone, water or a mixture of water and a polar solvent.

Bases that can be used include carbonates, such as sodium carbonate, potassium carbonate or calcium carbonate, and metal hydroxides, such as sodium hydroxide or potassium hydroxide.

The temperature of the reaction falls within room temperature and the boiling point of the particular solvent or solvent mixture. The reaction time lies between 0.5 and 36 hours.

When converting an ester in which $R^1$ is benzyl to the free acid a catalytic reduction (hydrogenation) can also be used.

Suitable solvents for process variant (iii) include hydrocarbons, such as benzene, toluene or xylene, halogenated hydrocarbons, such as methylene chloride or chloroform, alcohols, such as methanol, ethanol or isopropanol, ethers, such as for example diethyl ether, diisopropyl ether, tetrahydrofuran or 1,4-dioxane, ketones, such as acetone or methyl ethyl ketone, esters, such as methyl acetate or ethyl acetate, or nitriles, such as acetonitrile.

Bases that can be used include an alkali metal, such as sodium or potassium, an alkali metal or alkaline earth metal hydride, such as sodium hydride, potassium hydride or calcium hydride, a carbonate, such as sodium carbonate, potassium carbonate or calcium carbonate, or a metal hydroxide, such as sodium hydroxide or potassium hydroxide. Organic ammonium bases that can be used include for example, ammonia an alkylamine (primary amine), a dialkylamine (secondary amine) or a trialkylamine (tertiary amine).

The temperature of the reaction falls within room temperature and the boiling point of the particular solvent or solvent mixture. The reaction time lies between 5 minutes and 10 hours.

Suitable solvents for process variant B) include hydrocarbons, such as benzene, toluene or xylene, halogenated hydrocarbons, such as methylene chloride or chloroform, ethers, such as for example diethyl ether, diisopropyl ether, tetrahydrofuran or 1,4-dioxane, ketones, such as acetone or methyl ethyl ketone, esters, such as methyl acetate or ethyl acetate, or polar aprotic solvents, such as dimethylformamide, dimethylacetamide or dimethyl sulphoxide, and other solvents, such as acetonitrile or water.

Bases that can be used include an alkali metal, such as sodium or potassium, an alkali metal or alkaline earth metal hydride, such as sodium hydride, potassium hydride or calcium hydride, a carbonate, such as sodium carbonate, potassium carbonate, sodium hydrogen carbonate or potassium hydrogen carbonate, or a metal hydroxide, such as sodium hydroxide or potassium hydroxide.

The temperature of the reaction falls within room temperature and the boiling point of the particular solvent or solvent mixture. The reaction time lies between 5 minutes and 24 hours.

The process variant C) is preferably carried out in an aprotic solvent, such as benzene, toluene, xylene, tetrahydrofuran, diethyl ether, hexane, dimethylformamide, dimethylacetamide or dimethyl sulphoxide. For deprotinating the compound of general formula X, a base, such as sodium hydride, potassium tert-butylate or lithium diisopropylamide can be used.

The temperature of the reaction lies between $-78°$ C. and the boiling point of the particular solvent or solvent mixture. The reaction time lies between 0.5 and 24 hours.

Compounds of general formula X are described in the literature or can be prepared by methods analogous to those described in the literature. (Khim.-Farm. Zh. 16 (8), 931-4 [1982]; Ukr. Khim. 2 h. (Russ. Ed) 49 (11), 1205-8 [1983]; Fizol. Akt. Veshchestva 18. 75-9 [1986]; and USSR Patent 791746).

The compounds of the invention prepared by these processes can be isolated from the reaction mixtures in conventional manner, for example by distillation of the solvent at normal or reduced pressure, by precipitation with water or by extraction.

A higher level of purity can be achieved as a rule by column chromatography as well as by fractional distillation or crystallisation.

The compounds of the invention are, as a rule, colourless and odourless liquids or crystals that are soluble in water, slightly soluble in aliphatic hydrocarbons such as petroleum ether, hexane, pentane and cyclohexane and highly soluble in halogenated hydrocarbons, such as chloroform, methylene chloride and carbon tetrachloride, aromatic hydrocarbons, such as benzene, toluene and xylene, ethers, such as diethyl ether, tetrahydrofuran and dioxane, nitriles, such as acetonitrile, alcohols, such as methanol and ethanol, amides, such as dimethylformamide, and sulphoxides, such as dimethyl sulphoxide.

The compounds of the invention show a good herbicidal activity in broad leaved weeds and grasses. A selective use in various crops is possible, for example in such as rape, beets, soya beans, cotton, rice, barley, wheat and other cereals. Individual active substances are particularly suitable as selective herbicides in beet, cotton, soya and cereals. However the compounds can be used for control of weeds in permanent crops, such as for example forestry, ornamental trees, fruit, vine, citrus, nut, banana, coffee, tea, rubber, oil palm, cocoa, berry fruit and hop plantations and for the selective control of weeds in annual crops.

The compounds of the invention can used for example against the following plant species:

Dicotyledonous weeds of the species Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.

Monocotyledonous weeds of the species Avena, Alopecurus, Echinochloa, Setaria, Panicum, Digitaria, Poa, Eleusine, Brachiaria, Lolium, Bromus, Cyperus, Agropyron, Sagittaria, Monocharia, Fimbristylis, Eleocharis, Ischaemum and Apera.

The rates of use vary depending on the manner of pre- and postemergent use between 0.001 and 5 kg/ha.

The compounds of the invention can also be used as defoliants, desiccants and as total herbicides. They also influence plant growth and can thus be used to influence plant growth of crops. Some compounds also show fungicidal activity.

The compounds of the invention can be used either alone or in admixture with one another or with other active agents. Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 38, No. 3 (1989) under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example aliphatic and aromatic hydrocarbons, such as benzene, toluene, xylene, cyclohexanone, isophorone, dimethyl sulphoxide, dimethylformaide and other mineral-oil fractions and plant oils.

Suitable solid carriers include mineral earths, e.g. bentonite, silica gel, talc, kaolin, attapulgite, limestone, silicic acid and plant products, e.g. flours.

As surface-active agents there can be used for example calcium lignosulphonate, polyoxyethylenealkylphenyl ethers, naphthalenesulphonic acids and their salts, phenolsulphonic acids and their salts, formaldehyde condensates, fatty alcohol sulphates, as well as substituted benzenesulphonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual componets can be mixed just before use for example by the so-called commonly used tank-mixing method.

Formulations can be prepared, for example, from the following ingredients.

A) WETTABLE POWDER

1)

25 percent by weight active ingredient
60 percent by weight kaolin
10 percent by weight silicic acid
5 percent by weight of a mixture of calcium lignosulphonate and the sodium salt of N-methyl-N-oleyltaurine

2)

40 percent by weight active ingredient
25 percent by weight bentonite
25 percent by weight colloidal silicic acid
10 percent by weight of a mixture of calcium lignosulphonate and alkylphenyl polyglycol ether

B) PASTE 45 percent by weight active ingredient
5 percent by weight sodium aluminum silicate
15 percent by weight cetyl polyglycol ether with 8 mol of ethylene oxide
2 percent by weight spindle oil
10 percent by weight polyethylene glycol
23 percent by weight water

C) EMULSIFIABLE CONCENTRATE 25 percent by weight active ingredient
15 percent by weight cyclohexanone
55 percent by weight xylene
5 percent by weight of a mixture of calcium dodecylbenzenesulphonate and nonylphenolpolyoxyethylene.

The following Examples illustrate the preparation of compounds of the invention.

EXAMPLE 1

Methyl 2-(3-methoxyphenyl)-2-(4,6-dimethoxy-2-pyrimidinyloxy)acetate 8 g (230 mmol) Methyl 2-(3-methoxyphenyl)glycolate was dissolved in 100 ml dimethylformamide and treated with 2.8 g (20.4 mmol) potassium carbonate. After 20 minutes stirring, 8.8 g (40.7 mmol) 4,6-dimethoxy-2-methylsulphonylpyrimidine was added and the mixture heated for 1 hour at 90° C. The reaction mixture was then poured into 100 ml water and extracted with 100 ml ethyl acetate. The combined ethyl acetate phase was washed with water, dried over magnesium sulphate and evaporated. The residue was recrystallised from diisopropyl ether.

Yield: 9.8 g=73% of theory
mp: 97°–100° C.

EXAMPLE 2

2-(4,6-dimethoxy-2-pyrimidinyloxy)-2-phenylacetic acid 5 g (16 mmol) Methyl 2-(4,6-dimethoxy-2-pyrimidinyloxy)-2-phenylacetate was dissolved in 50 ml water/ethanol (1:1) and treated with 0.9 g potassium hydroxide. After stirring for 16 hours at room temperature, the mixture was extracted with ethyl acetate. The aqueous phase was acidified with 10% hydrochloric acid until it was pH 2 and extracted with ethyl acetate. After drying over magnesium sulphate, the ethyl acetate phase was concentrated the solid residue recrystallised from diisopropyl ether/ethyl acetate mixture.

Yield: 2.45 g=51% of theory
mp: 158°–161° C.

EXAMPLE 3

Methyl 2-(4,6-dimethoxy-2-pyrimidinylthio)-4-pentenoate 1.22 g (12.2 mmol) Diisopropylamine was dissolved in 10 ml tetrahydrofuran under nitrogen and treated with 7.8 ml (12.2 mmol) 1.6M n-butyllithium in hexane at a temperature between −78° and −50° C. The mixture was stirred for 20 minutes and then a solution of 3 g (12.2 mmol) methyl 2-(4,6-dimethoxy-2-pyrimidinylthio)acetate in 30 ml tetrahydrofuran was added to the reaction mixture and the mixture then stirred for 30 minutes. 1.45 g (12.2 mmol) 3-Bromopropene was added, dropwise, to the solution. The reaction mixture was slowly allowed to reach room temperature, with stirring, and then stirred for 20 hours. The mixture was added to 100 ml ice/water and extracted with ethyl acetate. The ethyl acetate phase, after drying over magnesium sulphate, was evaporated and then purified by medium pressure chromatography using hexane/ethyl acetate as eluent.

Yield: 0.9 g=25.9% of theory
$n_D^{20}$: 1.5342

PREPARATION OF THE STARTING MATERIAL FOR EXAMPLE 3

Methyl 2-(4,6-dimethoxy-2-pyrimidinylthio)acetate 25 g (230 mmol) Methyl thioglycolate was dissolved in 250 ml dimethylformamide and treated with 16.3 g (115 mmol) potassium carbonate. After 20 minutes stirring at room temperature, 50 g (2.3 mmol) 4,6-dimethoxy-2-methylsulphonylpyrimidine was added and the mixture heated for 3 hours at 90° C. The reaction mixture was then poured into water and extracted with ethyl acetate. The organic phase was washed with water and dried over magnesium sulphate. The solvent was distilled and the resulting crude product was rerystallised from diisopropyl ether.

Yield: 44.6 g = 79.4% of theory
mp: 67°-69° C.

EXAMPLE 4

Methyl 2-(4,6-dimethoxy-2-pyrimidinyloxy)-3-fluoro-3-methylbutanoate 4 g (26.6 mmol) Methyl 3-fluoro-2-hydroxy-3-methylbutanoate and 5.81 g (26.6 mmol) 4,6-dimethoxy-2-methylsulphonylpyrimidine were dissolved in 75 ml dimethylformamide at 20° C. and treated with 1.84 g (13.3 mmol) potassium carbonate. The suspension was stirred for 5 hours at 20° C. and heated for one hour at 60° C. The reaction mixture was then poured into 150 ml ice-water and extracted with three lots of 75 ml ethyl acetate. The combined ethyl acetate phase was washed with water, dried over magnesium sulphate, filtered and evaporated. The solid residue was purified by silica gel column chromatography using hexane/ethyl acetate as eluent.

Yield: 2.9 g = 37.7% of theory
mp: 73°-74° C.

EXAMPLE 5

2-(4,6-Dimethoxy-2-pyrimidinyloxy)-3-fluoro-3-methylbutanoic acid 2 g (6.9 mmol) Methyl 2-(4,6-dimethoxy-2-pyrimidinyloxy)-3-fluoro-3-methylbutanoate was dissolved in a mixture of 20 ml water and 10 ml methanol and treated with 387 mg (6.9 mmol) potassium hydroxide. After stirring for 4 hours at 50° C., the mixture was added to 50 ml water and extracted with 50 ml ethyl acetate. The aqueous phase was acidified with hydrochloric acid until it was pH 2 and extracted with three lots of 100 ml ethyl acetate. The combined ethyl acetate phase was washed with water, dried over magnesium sulphate, filtered and evaporated.

Yield: 1.0 g = 54.5% of theory
mp: 107°-108° C.

In a similar manner, the following compounds of the invention of general formula I were prepared:

| Example No. | A | $R^1$ | $R^2$ | $R^3$ | X | Y | Physical constant |
|---|---|---|---|---|---|---|---|
| 6 | 3-Pyridyl | H | $OCH_3$ | $OCH_3$ | O | CH | mp.: 191-193° C. |
| 7 | 2-(N-Methyl)-indolyl | $CH_3$ | $OCH_3$ | $OCH_3$ | O | CH | mp.: 148-149° C. |
| 8 | Phenyl | $C(CH_3)_3$ | $OCH_3$ | $OCH_3$ | O | CH | mp.: 126-127° C. |
| 9 | 3-Methoxyphenyl | H | $OCH_3$ | $OCH_3$ | O | CH | mp.: 141-144° C. |
| 10 | 4-Methoxyphenyl | $CH_3$ | $OCH_3$ | $OCH_3$ | O | CH | mp.: 91-92° C. |
| 11 | 4-Methoxyphenyl | H | $OCH_3$ | $OCH_3$ | O | CH | mp.: 132-133° C. |
| 12 | Phenyl | $CH_3$ | $OCH_3$ | $OCH_3$ | O | CH | mp.: 89-90° C. |
| 13 | Phenyl | $CH_3$ | $OCH_3$ | $OCH_3$ | O | CH | mp.: 80-81° C. (S-Isomer) |
| 14 | Phenyl | H | $OCH_3$ | $OCH_3$ | O | CH | mp.: 153-154° C. (S-Isomer) |
| 15 | Phenyl | $CH_3$ | $OCH_3$ | $OCH_3$ | O | CH | mp.: 83-84° C. (R-Isomer) |
| 16 | Phenyl | H | $OCH_3$ | $OCH_3$ | O | CH | mp.: 148-149° C. (R-Isomer) |
| 17 | 2-Thienyl | $CH_2CH_3$ | $OCH_3$ | $OCH_3$ | O | CH | mp.: 87-88° C. |
| 18 | 2-Thienyl | H | $OCH_3$ | $OCH_3$ | O | CH | mp.: 136-137° C. |
| 19 | Phenyl | $CH_2CH_3$ | $OCH_3$ | $OCH_3$ | O | CH | mp.: 82-84° C. |
| 20 | 4-Fluorophenyl | $CH_3$ | $OCH_3$ | $OCH_3$ | O | CH | mp.: 92-95° C. |
| 21 | 4-Fluorophenyl | H | $OCH_3$ | $OCH_3$ | O | CH | mp.: 134-138° C. |
| 22 | 3-Pyridyl | $CH_2CH_3$ | $OCH_3$ | $OCH_3$ | O | CH | mp.: 66-67° C. |
| 23 | Phenyl | $CH_3$ | $SCH_3$ | $SCH_3$ | O | N | mp.: 79-81° C. |
| 24 | 2,6-Difluorophenyl | $CH_3$ | $OCH_3$ | $OCH_3$ | O | CH | mp.: 78-80° C. |
| 25 | 2,6-Difluorophenyl | H | $OCH_3$ | $OCH_3$ | O | CH | mp.: 189-192° C. |
| 26 | 4-Trifluoromethylphenyl | $CH_3$ | $OCH_3$ | $OCH_3$ | O | CH | mp.: 117-119° C. |
| 27 | 4-Trifluoromethylphenyl | H | $OCH_3$ | $OCH_3$ | O | CH | mp.: 152-155° C. |
| 28 | 3-Thienyl | $CH_2CH_3$ | $OCH_3$ | $OCH_3$ | O | CH | mp.: 94-95° C. |
| 29 | 3-Thienyl | H | $OCH_3$ | $OCH_3$ | O | CH | mp.: 147-148° C. (dec.) |
| 30 | 4-Bromophenyl | $CH_3$ | $OCH_3$ | $OCH_3$ | O | CH | mp.: 104-105° C. |
| 31 | 4-Bromophenyl | H | $OCH_3$ | $OCH_3$ | O | CH | mp.: 168-170° C. |
| 32 | 3,5-Di- | $CH_3$ | $OCH_3$ | $OCH_3$ | O | CH | mp.: 125-126° C. |

-continued

| Example No. | A | R¹ | R² | R³ | X | Y | Physical constant |
|---|---|---|---|---|---|---|---|
| | fluorophenyl | | | | | | |
| 33 | 3,5-di-fluorophenyl | H | OCH₃ | OCH₃ | O | CH | mp.: 128-131° C. |
| 34 | CH=CH₂ | CH₃ | OCH₃ | OCH₃ | O | CH | $R_f$-Value: 0,92 (in ethyl acetate) |
| 35 | CH=CH₂ | H | OCH₃ | OCH₃ | O | CH | $R_f$-Value: 0,26 (in ethyl acetate) |
| 36 | Phenyl | CH₃ | OCH₃ | NHCH₃ | O | N | foam mp.: >59° C. |
| 37 | Phenyl | CH₃ | CH₃ | NHCH₃ | O | N | mp.: 125-130° C. |
| 38 | Phenyl | CH₃ | OCH₃ | N(CH₃)₂ | O | N | mp.: 94-98° C. |
| 39 | CH₂—CH=CH₂ | " | OCH₃ | OCH₃ | S | CH | mp.: 91-94° C. |
| 40 | Phenyl | Benzyl | OCH₃ | OCH₃ | O | CH | mp.: 123-124° C. |
| 41 | 2-Naphthyl | CH₃ | OCH₃ | OCH₃ | O | CH | mp.: 129-130° C. |
| 42 | 2-Naphthyl | H | OCH₃ | OCH₃ | O | CH | mp.: 170-171° C. |
| 43 | 1-Naphthyl | CH₃ | OCH₃ | OCH₃ | O | CH | mp.: 126-127° C. |
| 44 | 1-Naphthyl | H | OCH₃ | OCH₃ | O | CH | mp.: 169-171° C. |
| 45 | Phenyl | H | CH₂CH₃ | CH₂CH₃ | O | CH | mp.: 135-137° C. |
| 46 | Phenyl | CH₃ | OCH₃ | OCH₃ | S | CH | mp.: 94-95° C. |
| 47 | Phenyl | H | OCH₃ | OCH₃ | S | CH | mp.: 158-160° C. |
| 48 | 2-Thienyl | CH₃ | OCH₃ | OCH₃ | O | CH | mp.: 101-103° C. |
| 49 | CH=CH—CH₃ | CH₃ | OCH₃ | OCH₃ | O | CH | mp.: 60-61° C. |
| 50 | CH=CH—CH₃ | H | OCH₃ | OCH₃ | O | CH | mp.: 126-128° C. |
| 51 | 2-Nitro-phenyl | CH₃ | OCH₃ | OCH₃ | O | CH | mp.: 103° C. |
| 52 | 2-Nitro-phenyl | H | OCH₃ | OCH₃ | O | CH | mp.: 162° C. |
| 53 | 2-Chloro-phenyl | CH₃ | OCH₃ | OCH₃ | O | CH | mp.: 118° C. |
| 54 | 2-Chloro-phenyl | H | OCH₃ | OCH₃ | O | CH | mp.: 180° C. |
| 55 | Phenyl | CH₃ | OCH₂CH₃ | OCH₂CH₃ | O | CH | mp.: 59-61° C. |
| 56 | Phenyl | H | SCH₃ | SCH₃ | O | CH | $N_D^{20}$: 1,5745 |
| 57 | Phenyl | H | OCH₂CH₃ | OCH₂CH₃ | O | CH | mp.: 158-160° C. |
| 58 | Cyclopropyl | CH₃ | OCH₃ | OCH₃ | O | CH | mp.: 83-84° C. |
| 59 | Cyclopropyl | H | OCH₃ | OCH₃ | O | CH | mp.: 147-148° C. |
| 60 | CF(CH₃)₂ | CH₂CH₃ | OCH₃ | OCH₃ | O | CH | mp.: 73-74° C. |
| 61 | CF(CH₃)-Phenyl | CH₂CH₃ | OCH₃ | OCH₃ | O | CH | mp.: 106° C. |
| 62 | C(CH₃)₂—(OCH₃) | CH₃ | OCH₃ | OCH₃ | O | CH | mp.: 102-103° C. |
| 63 | CCl(CH₃)₂ | CH₃ | OCH₃ | OCH₃ | O | CH | mp.: 109° C. |
| 64 | C(CH₃)₂—(OCH₃) | H | OCH₃ | OCH₃ | O | CH | mp.: 139-141° C. |
| 65 | CF(CH₃)₂ | CH₂CH₃ | OCH₃ | OCH₃ | O | N | $n_D^{20}$:1,4754 |
| 66 | CCl(CH₃)₂ | CH₂CH₃ | OCH₃ | OCH₃ | O | CH | mp.: 95-96° C. |
| 67 | 1-Fluoro-cyclohexyl | CH₃ | OCH₃ | OCH₃ | O | CH | mp.: 99-100° C. |
| 68 | CF(CH₃)-Phenyl | CH₂CH₃ | OCH₃ | OCH₃ | O | N | mp.: 79-80° C. |
| 69 | 1-Methoxy-cyclopentyl | CH₃ | OCH₃ | OCH₃ | O | CH | mp.: 72-75° C. |
| 70 | 1-Methoxy-cyclohexyl | CH₃ | OCH₃ | OCH₃ | O | CH | mp.: 128-130° C. |
| 71 | CF(CH₃)-Phenyl | H | OCH₃ | OCH₃ | O | CH | mp.: 135-136° C. |
| 72 | 1-Fluoro-cyclopentyl | CH₃ | OCH₃ | OCH₃ | O | CH | mp.: 89-90° C. |
| 73 | C(CH₂CH₃)—(CH₃)(OCH₃) | CH₃ | OCH₃ | OCH₃ | O | CH | mp.: 72-74° C. |
| 74 | C(OCH₂CH₃)—(CH₃)(Phenyl) | CH₂CH₃ | OCH₃ | OCH₃ | O | N | mp.: 71-72° C. |
| 75 | 1-Fluoro-cyclohexyl | H | OCH₃ | OCH₃ | O | CH | mp.: 140-141° C. |
| 76 | CHF-Phenyl | H | OCH₃ | OCH₃ | O | CH | $n_D^{20}$: 1.5374 |
| 77 | CHF-Phenyl | CH₂CH₃ | OCH₃ | OCH₃ | O | CH | mp.: 57-59° C. |
| 78 | CHF-Phenyl | H | OCH₃ | OCH₃ | O | N | |
| 79 | CHF-Phenyl | CH₂CH₃ | OCH₃ | OCH₃ | O | N | |
| 80 | CF(CH₃)-Phenyl | H | OCH₃ | OCH₃ | O | N | |
| 81 | C(OCH₂CH₃)—(CH₃)(Phenyl) | H | OCH₃ | OCH₃ | O | CH | mp.: 128-130° C. |
| 82 | C(OCH₂CH₃)—(CH₃)(Phenyl) | H | OCH₃ | OCH₃ | O | N | |
| 83 | C(OCH₂CH₃)—(CH₃)(Phenyl) | CH₂CH₃ | OCH₃ | OCH₃ | O | N | |
| 84 | CCl(CH₃)-Phenyl | H | OCH₃ | OCH₃ | O | CH | |
| 85 | CCl(CH₃) Phenyl | CH₂CH₃ | OCH₃ | OCH₃ | O | CH | mp.: 103-105° C. |

-continued

| Example No. | A | R¹ | R² | R³ | X | Y | Physical constant |
|---|---|---|---|---|---|---|---|
| 86 | CCl(CH$_3$)-Phenyl | H | OCH$_3$ | OCH$_3$ | O | N | |
| 87 | CCl(CH$_3$)-Phenyl | CH$_2$CH$_3$ | OCH$_3$ | OCH$_3$ | O | N | |
| 88 | CHF-Phenyl | H | OCH$_3$ | OCH$_3$ | S | CH | |
| 89 | CHF-Phenyl | CH$_2$CH$_3$ | OCH$_3$ | OCH$_3$ | S | CH | |
| 90 | CHF-Phenyl | H | OCH$_3$ | OCH$_3$ | S | N | |
| 91 | CHF-Phenyl | CH$_2$CH$_3$ | OCH$_3$ | OCH$_3$ | S | N | |
| 92 | CF(CH$_3$)-Phenyl | H | OCH$_3$ | OCH$_3$ | S | CH | |
| 93 | CF(CH$_3$)-Phenyl | CH$_2$CH$_3$ | OCH$_3$ | OCH$_3$ | S | CH | |
| 94 | CF(CH$_3$)-Phenyl | H | OCH$_3$ | OCH$_3$ | S | N | |
| 95 | CF(CH$_3$)-Phenyl | CH$_2$CH$_3$ | OCH$_3$ | OCH$_3$ | S | N | |
| 96 | 1-Fluoro-cyclopentyl | H | OCH$_3$ | OCH$_3$ | O | CH | mp: 138–140° C. |
| 97 | 1-Fluoro-cyclopentyl | CH$_3$ | OCH$_3$ | OCH$_3$ | O | N | |
| 98 | 1-Fluoro-cyclopentyl | H | OCH$_3$ | OCH$_3$ | O | N | |
| 99 | 1-Fluoro-cyclohexyl | CH$_3$ | OCH$_3$ | OCH$_3$ | O | N | $n_D^{20}$: 1.4963 |
| 100 | 1-Fluoro-cyclohexyl | H | OCH$_3$ | OCH$_3$ | O | N | |
| 101 | CF(CH$_3$)$_2$ | H | OCH$_3$ | OCH$_3$ | O | N | $n_D^{20}$: 1.4747 |
| 102 | C(CH$_2$CH$_3$)—(CH$_3$)(OCH$_3$) | H | OCH$_3$ | OCH$_3$ | O | CH | mp: 137–140° C. |
| 103 | 1-Methoxy-cyclopentyl | H | OCH$_3$ | OCH$_3$ | O | CH | mp: 150–153° C. |

The following examples illustrate the possibilities for use of the compounds of the invention.

EXAMPLE A

In a greenhouse, the noted plant species were treated post-emergently with the noted compounds of the invention, at a rate of 0.1 kg active ingredient/ha. The compounds of the invention were sprayed evenly over the plants as emulsions or suspensions in 500 liters water/ha. Two weeks after the treatment, the compounds of the invention showed a high crop selectivity in wheat and maize with excellent activity against the weeds. The comparison material did not show similar high efficacy.

In the following table:
0 = no damage
1 = 1–24% damage
2 = 25–74% damage
3 = 75–89% damage
4 = 90–100% damage
HELAN = Helianthus annuus
ABUTH = Abutilon theophrasti
GALAP = Galium aparine
SEBEX = Sesbania exaltata
SOLSS = Solanum sp.
VERPE = Veronica persica

EXAMPLE B

In a greenhouse, the noted plant species were treated pre-emergently with the noted compounds of the invention, at a rate of 1.0 kg active ingredient/ha. The compounds of the invention were sprayed evenly over the soil as emulsions or suspensions in 500 liters water/ha. Three weeks after the treatment, the compounds of the invention showed a high crop selectivity in soya-beans, cotton, sunflowers, wheat and maize with excellent activity against the weeds. The comparison material did not show similar high efficacy.

In the following table:
0 = no damage
1 = 1–24% damage
2 = 25–74% damage
3 = 75–89% damage
4 = 90–100% damage
GLMXA = Glycine maxima
GOSHI = Gossypium hirsutum
HELAN = Helianthus annuus
TRZAX = Triticum aestivum
ZEAMX = Zea mays
PANSS = Panicum maximum
GALAP = Galium aparine
SOLSS = Solanum sp.
VERPE = Veronica persica

| Compound of the Invention | HELAN | ABUTH | GALAP | SEBEX | SOLSS | VERPE |
|---|---|---|---|---|---|---|
| Example 12 | 1 | 3 | 3 | 3 | 3 | 3 |
| Example 49 | 0 | 3 | 3 | 2 | 3 | 3 |
| Example 50 | 1 | 3 | 3 | 3 | 3 | 3 |
| Untreated | 0 | 0 | 0 | 0 | 0 | 0 |
| Comparison | | | | | | |
| Methyl 2-(4-isopropyl-4-methyl-5-oxo-2-imidazolin-2-yl)-4(5)-methylbenzoate | 3 | 2 | 3 | 2 | 3 | 2 |

| Compound of the Invention | GLXMA | GOSHI | HELAN | TRZAX | ZEAMX | PANSS | GALAP | SOLSS | VERPE |
|---|---|---|---|---|---|---|---|---|---|
| Example 12 | 1 | 0 | 1 | 0 | 1 | 3 | 3 | 4 | 3 |
| Example 48 | 1 | 0 | 0 | 0 | — | — | 3 | 3 | 4 |
| Untreated Comparison | 0 | 0 | 0 | 0 | 0 | 0 | 0 | 0 | 0 |
| Methyl 2-(4-isopropyl-4-methyl-5-oxo-2-imidazolin-2-yl)-4(5)-methylbenzoate | 3 | 2 | 3 | 2 | 3 | 3 | 4 | 4 | 3 |

EXAMPLE C

In a greenhouse, the compound shown in the table was applied at the rates given. For this the compounds were applied in vessels containing 1500 ml water. The test plants there were treated at the 2 to 5 leaved stage. Three weeks after the treatment, the damage to the plants was estimated. The compound of the invention showed strong activity against important rice weeds with good selectivity in paddy rice.

In the following Table:

4 = 90–100% damage
AVEFA = *Avena fatua*
SETVI = *Setaria viridis*
CYPES = *Cyperus esculentus*
ABUTH = *Abutilon theophrasti*
IPOSS = *Ipomoea purpurea*
MATCH = *Matricaria chamomilla*
POLSS = Polygonum sp.
SOLSS = Solanum sp.
VERPE = *Veronica persica*
VIOSS = Viola sp

| Compound of the Invention | AVEFA | SETVI | CYPES | ABUTH | IPOSS | MATCH | POLSS | SOLSS | VFRPE | VIOSS |
|---|---|---|---|---|---|---|---|---|---|---|
| Example 4 | 3 | 4 | 4 | 3 | 3 | 3 | — | — | — | — |
| Example 5 | 3 | 4 | 4 | 3 | 3 | 4 | — | — | — | — |
| Example 15 | 3 | 4 | 3 | 3 | 3 | 4 | 3 | 3 | 4 | 4 |
| Example 28 | 3 | 3 | 3 | — | 3 | — | 3 | 3 | 3 | 4 |
| Example 58 | — | 3 | 3 | 3 | 3 | 3 | — | — | — | — |
| Example 59 | — | 4 | 3 | 3 | 3 | 3 | — | — | — | — |
| Untreated | 0 | 0 | 0 | 0 | 0 | 0 | 0 | 0 | 0 | 0 |

0 = no damage
1 = slight damage
2 = medium damage
3 = heavy damage
4 = total destruction
ORYSA = *Oryza sativa*
ECHCG = *Echinochloa crus-galli*
SAGPY = *Sagittaria pygmaea*
SCPJU = *Scirpus juncoides*
MOOVA = *Monochoria vaginalis*
CYPSE = *Cyperus serotinus*

EXAMPLE E

In a greenhouse, the noted plant species were treated post-emergently with the noted compounds of the invention, at a rate of 0.1 kg active ingredient/ha. The compounds of the invention were sprayed evenly over the plants as emulsions in 500 liters water/ha. Two weeks after the treatment, the compounds of the invention showed a high crop selectivity in cotton with excellent activity against the weeds. The comparison material did not show similar high efficacy.

| Compound of the Invention | Water aplication kg active ingredient/ha | ORYSA | ECHCG | SAGPY | SCPJU | MOOVA | CYPSE |
|---|---|---|---|---|---|---|---|
| Example 12 | 1,0 | 0 | 3 | 4 | 4 | 4 | 4 |

EXAMPLE D

In a greenhouse, the noted plant species were treated pre-emergently with the noted compounds of the invention, at a rate of 1.0 kg active ingredient/ha. The compounds of the invention were sprayed evenly over the soil as emulsions or suspensions in 500 liters water/ha. Three weeks after the treatment, the compounds of the invention showed excellent activity against the weeds.

In the following table:
0 = no damage
1 = 1–24% damage
2 = 25–74% damage
3 = 75–89% damage In the following table:
0 = no damage
1 = 1–24% damage
2 = 25–74% damage
3 = 75–89% damage
4 = 90–100% damage
GOSHI = *Gossypium hirsutum*
ALOMY = *Alopecurus myosuroides*
PANSS = *Panicum maximum*
ABUTH = *Abutilon theophrasti*
IPOSS = *Ipomea purpurea*
POLSS = Polygonum sp.
SOLSS = Solanum sp.
VERPE = *Veronica persica*
VIOSS = Viola sp

| Compound of the Invention | GOSHI | ALOMY | PANSS | ABUTH | IPOSS | POLSS | SOLSS | VERPE | VIOSS |
|---|---|---|---|---|---|---|---|---|---|
| Example 4 | 1 | 3 | 3 | 4 | 3 | 3 | 3 | 3 | 3 |
| Untreated Comparison | 0 | 0 | 0 | 0 | 0 | 0 | 0 | 0 | 0 |
| (EP 0 347 811) Compound No. 243 | 0 | 1 | 1 | 1 | 0 | 1 | 2 | 1 | 0 |

EXAMPLE F

In a greenhouse, the noted plant species were treated post-emergently with the noted compounds of the invention, at a rate of 0.1 kg active ingredient/ha. The compounds of the invention were sprayed evenly over the plants as emulsions in 500 liters water/ha. Two weeks after the treatment, the compounds of the invention showed a high crop selectivity in cotton with excellent activity against the weeds. The comparison material did not show similar high efficacy.

In the following table:
0 = no damage
1 = 1–24% damage
1 = 25–74% damage
3 = 75–89% damage
4 = 90–100% damage
GOSHI = *Gossypium hirsutum*
AGRRE = *Elymus repens*
BROTE = *Bromus tectorum*
SETVI = *Setaria viridis*
PANSS = *Panicum maximum*
SORHA = *Sorghum halepense*
ABUTH = *Abutilon theophrasti*
GALAP = *Galium aparine*
IPOSS = *Ipomea purpurea*
MATCH = *Matricaria chamomilla*
POLSS = *Polygonum sp.*
SEBEX = *Sesbania exaltata*
VERPE = *Veronica persica*

| Compound of the Invention | GOSHI | AGREE | BROTE | SETVI | PANSS | SORHA | ABUTH | GALAP | IPOSS | MATCH | POLSS | SEBEX | VERPE |
|---|---|---|---|---|---|---|---|---|---|---|---|---|---|
| Example 5 | 1 | 3 | 3 | 3 | 3 | 3 | 3 | 3 | 3 | 3 | 4 | 4 | 3 |
| Untreated Comparison | 0 | 0 | 0 | 0 | 0 | 0 | 0 | 0 | 0 | 0 | 0 | 0 | 0 |
| (EP 0 347 811) Compound No. 4 | 0 | 1 | 0 | 2 | 2 | 2 | 0 | 2 | 0 | 0 | 1 | 2 | 2 |

We claim:

1. Compound of the formula

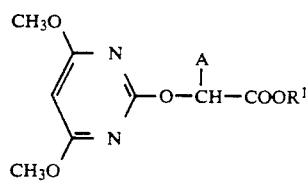

in which $R^1$ is hydrogen or $C_1$–$C_4$ alkyl and A is $C_3$ alkyl or cyclopentyl each of which is substituted in the 1-position by fluorine.

2. Compound according to claim 1 which is 2-(4,6-dimethoxy-2-pyrimidinyloxy)-3-fluoro-3-methyl-butanoic acid or the methyl ester thereof.

3. Compound according to claim 1 in which $R^1$ is hydrogen, methyl or ethyl.

4. Compound according to claim 1 in which A is 1-cyclopentyl.

5. Compound according to claim 4 in which $R^1$ is hydrogen.

6. Compound of the formula

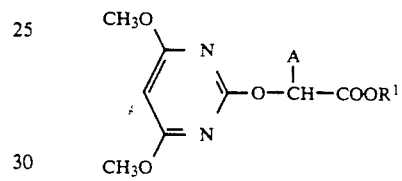

in which $R^1$ is hydrogen, $C_1$–$C_4$ alkyl or benzyl and A is ($\alpha$-methyl) benzyl substituted in the 1-position by fluorine.

7. A herbicidal composition which comprises a compound according to claim 1, in admixture with agriculturally acceptable carriers or diluents.

8. A herbicidal composition which comprises a compound according to claim 2, in admixture with agriculturally acceptable carriers or diluents.

9. A herbicidal composition which comprises a compound according to claim 3, in admixture with agriculturally acceptable carriers or diluents.

10. A method of combating weeds which comprises applying to the weeds or their locus an effective amount of a compound according to claim 1.

11. A method of combating weeds which comprises applying to the weeds or their locus an effective amount of a compound according to claim 2.

12. A method of combating weeds which comprises applying to the weeds or their locus an effective amount of a compound according to claim 3.

* * * * *